United States Patent [19]

Swon et al.

[11] Patent Number: 4,658,631

[45] Date of Patent: Apr. 21, 1987

[54] FRIABILITY DRUM TESTER FOR PHARMACEUTICAL TABLETS

[76] Inventors: James E. Swon, 12 Twin Park Dr., Brookside, N.J. 07926; Glen W. Hill, 28 Marion St., Port Reading, N.J. 07064

[21] Appl. No.: 846,937

[22] Filed: Apr. 1, 1986

[51] Int. Cl.⁴ .............................................. G01N 3/56
[52] U.S. Cl. .......................................... 73/7; 73/78; 73/866
[58] Field of Search ............. 73/432 Z, 432 R, 432 K, 73/78, 7

[56] References Cited

U.S. PATENT DOCUMENTS

| | | | |
|---|---|---|---|
| 1,459,143 | 6/1923 | Curran | 73/78 X |
| 2,550,802 | 5/1951 | Gholson | 73/78 X |
| 3,618,395 | 11/1971 | Melliger | 73/432 Z |
| 3,757,566 | 9/1973 | Flury | 73/78 |
| 3,766,776 | 10/1973 | Williams | 73/78 |
| 3,943,757 | 3/1976 | Wilhelm, Jr. | 73/78 |
| 4,022,056 | 5/1977 | Barland | 73/78 |
| 4,143,539 | 3/1979 | Baillie | 73/7 |
| 4,542,646 | 9/1985 | Smith et al. | 73/78 |

FOREIGN PATENT DOCUMENTS

| | | | |
|---|---|---|---|
| 3312942 | 10/1984 | Fed. Rep. of Germany | 73/7 |
| 3329735 | 11/1984 | Fed. Rep. of Germany | 73/7 |
| 684396 | 9/1979 | U.S.S.R. | 73/7 |
| 729486 | 4/1980 | U.S.S.R. | 73/7 |
| 773477 | 10/1980 | U.S.S.R. | 73/7 |
| 879372 | 11/1981 | U.S.S.R. | 73/7 |

*Primary Examiner*—Michael J. Tokar
*Assistant Examiner*—Tom Noland

[57] ABSTRACT

A tester of resistance of separate batches of tablets to breakage including a revolvable cylinder revolvable around a central height axis that extends axially of the cylinder, cylindrical space formed therein being divided into separate spaces by dividing walls extending radially across a diameter of the inner cylindrical space and the dividing walls for each space having a radially extending concave surface along one radius and a convex surface along another radius such that in each of the separate spaces there is formed a scoop facilitating collecting and tossing groups of tablets as the cylindrical cylinder revolves, and the revolvable cylinder including an access opening-structure for separate insertion and removal of tablets from the separate spaces before and after tumbling. The revolvable cylinder includes as a part of its combination, a motor mechanism for intermittently revolving the cylinder, and a male-female connection for mounting and dismounting in association with the motor mechanism. Also, the access opening-structure is preferably in the nature of a lid having central male or female structure that mates with an opposite female or male structure extending axially of the cylinder, facilitating the securing of the lid. Also, the edge of the lid is preferably stepped, to partially fit within space of the cylinder when mounted thereon, improving the securing of the lid onto the cylinder.

10 Claims, 2 Drawing Figures

FRIABILITY DRUM TESTER FOR PHARMACEUTICAL TABLETS

This invention relates to a novel tester of batches of pharmaceutical tablets with regard to friability thereof.

BACKGROUND TO THE INVENTION

Prior to the present invention, there have been inadequacies in available apparatus and/or mechanisms to quickly and reliably and/or inexpensively and/or accurately ascertain real susceptibility of new batches of tablets to breakage and general wear and tear during handling, shipping, merchandizing and use by the consumer.

Even though a particular apparatus might give a good and proper test for a batch being tested, it has not been readily possible have more than one sample of tablets be tested from each new batch of tableted tablets, as a test of consistent results as between the different tablets, nor to achieve concurrent testing, in absence of expensive duplication of machines and/or excessive expenditures of time required for repeat testing.

Another difficulty or disadvantage has been the absense of a simple and inexpensive structure.

Another difficulty or disadvantage has been the absence of a structure not bulky, nor easy to handle and simple to operate.

Another difficulty or disadvantage has been the absence of a light weight but sturdy testing structure.

Another difficulty or disadvantage has been the absense of a portable friability tester adapted to tests groups of tablets as one sample while concurrently testing therewith a separate group of other tablets as one or more other samples.

Another difficulty or disadvantage has been the absence of a friability tablet tester for multiple sample testing concurrently, which is adapted to be brokendown into a separate portable tumbler-container apart from driving mechanism therefor.

Another difficulty or disadvantage has been the absence of an apparatus for tablet friability simultaneously testing by the same apparatus, of different segregated samples of tablets, of which there is convenient access-opening detachably securable thereon to segregated spaces thereof.

OBJECTS

An object of the present invention is to obtain a novel combination overcoming and/or avoiding one or more of the preceding difficulties and/or disadvantages.

Another more particular object is to obtain a novel combination making possible simultaneous friability testing by the same combination separate segregated samples of tablets from the same and/or different batches.

Another more particular object is to obtain such novel combination for friability testing of tablets simultaneously for segregated samples, of light weight and non-bulky size adaptable for portable handling thereof.

Another object is to obtain such combination having novel segregating inner walls segregating a plurality of separate tumbler spaces, of which the segregating wall(s) is/are characterized by shape(s) adapted to improved collection and tumbling of the sample of tablet(s) therein.

Another object is to obtain such novel combination for tablet friability testing of segregated samples simultaneously by the same novel combination, including a mechanism for easy and quick access to segregated spaced thereof for inserting and/or withdrawing the segregated samples.

Other objects become apparent from the preceding and following disclosure.

These objects are obtained by the invention as described herein.

SUMMARY OF THE INVENTION

Broadly the present invention may be described as a novel combination inclusive of a revolvable drum of which inner circumscribing walls thereof form a plurality of separate segregated spaces by one or more partitioning walls. The separate segregated spaces are totally enclosed apart from access-opening structure for separate insertion into and withdrawal from the separate spaces the separate tablet(s) to be tested by tumbling for their friability characteristics. The combination also includes appropriate mechanical means for controllably revolving the drum.

In one preferred embodiment, one or more of the partitioning wall(s) forming the separate segregated spaces extend from and/or through a center of the total space with partitioning wall(s) anchored on substantially opposing faces of the inner surface(s) of the revolvable drum.

In another preferred embodiment, the access-opening structure forms an open top vessel with opening(s) thereof to each of the separate segregated spaces and a lid thereto for intertermittently effectively and securely closing and opening the opening.

In another preferred embodiment, the lid above-noted includes stepped structure of which the stepped structure is adapted for intermittently detachably fitting securely against the inner surface(s) of drum such that the lid is less susceptable to fall-off during the revolving of the drum.

In another preferred embodiment, the lid has one of a male or female structure on an inner face thereof and the drum has a correspondingly positioned other female or male structure adapted to intermittently detachably secure the lid onto the vessel such that the lid is less susceptable to fall-off furing the revolving of the drum.

In another preferred embodiment, the drum is cylindrically shaped as a cylinder, and is adapted to revolve around an axis of rotation extending substantially concentrically of a height central axis of the cylinder, and the partitioning wall(s) extend(s) substantially along a diameter of the cylinder.

In another preferred embodiment, the drum includes one of a male and female structure on one end of the drum or cylinder, and the rotation mechanism and structure thereof includes another and mating other female or male structure, such that the drum or cylinder is intermittently detachable and separable from the rotation mechanism and structure thereof.

In another preferred embodiment, the rotation mechanism includes a motor adapted to rotate the drum or cylinder around a height central axis of the drum or cylinder.

In another preferred embodiment, utilizing the cylinder as the drum, the partitioning wall extends substantially straight across the inner space along a diameter of the cylinder, forming two segregated subspaces of substantially equal volume.

In another preferred embodiment, the partitioning wall(s) are shaped such that the face of at-least one radius-length of the partitioning wall of the cylinder, is of concave shape in the nature of a scoop facilitating collection of the tablets into a group prior to the tumbling of the tablets during the rotation of the drum by the revolving mechanism and structure thereof. Typically in this preferred embodiment, the opposite face of the wall forming the concave surface, is convex and in an adjacent segregated subspace.

The invention may be better understood by making reference to the following Figures.

THE FIGURES

FIG. 1 illustrates diagrammatically a side view of the cylindrical drum and top thereof, in partial cut-away and partial cross-section.

FIG. 2 illustrtes diagrammatically a side-view of the drum and lid and revolving structures and motor, as taken along line 2—2 of FIG. 1, in partial cut-away and partial cross-section.

DETAILED DESCRIPTION

Figure 1:
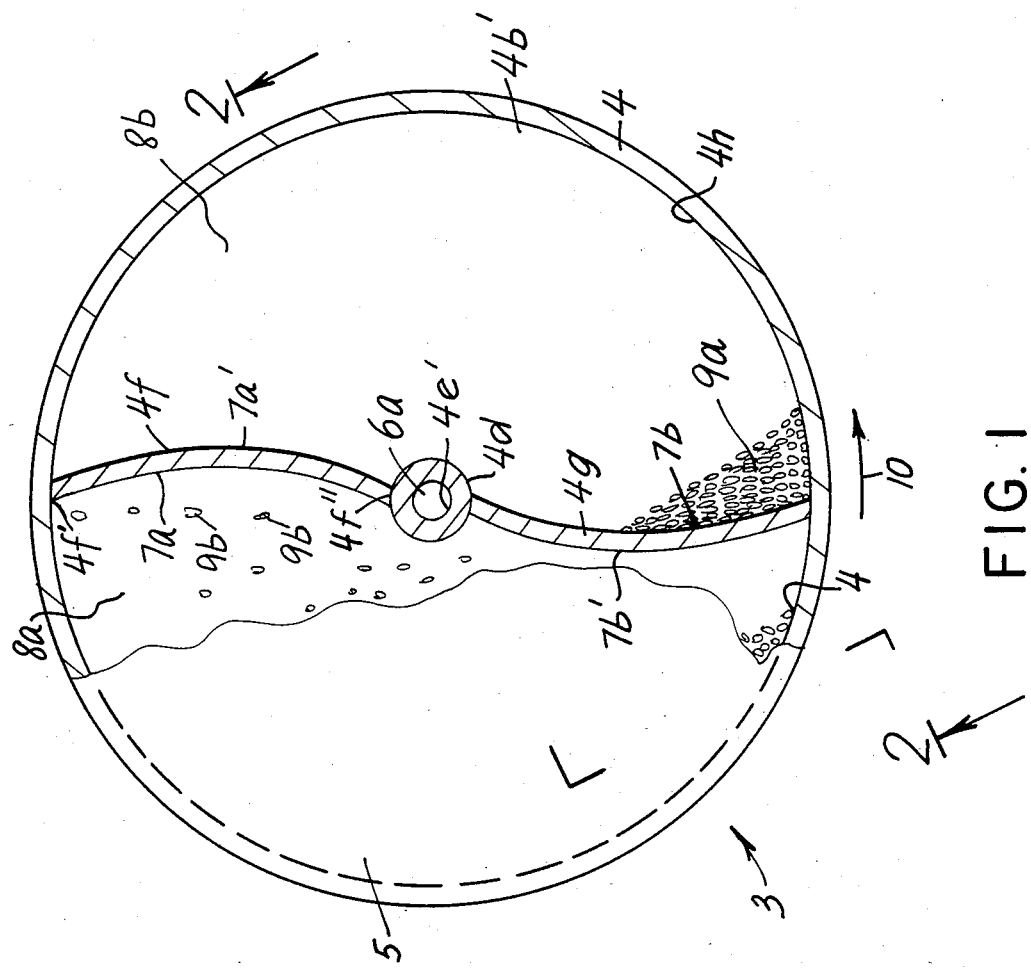
Figure 2:
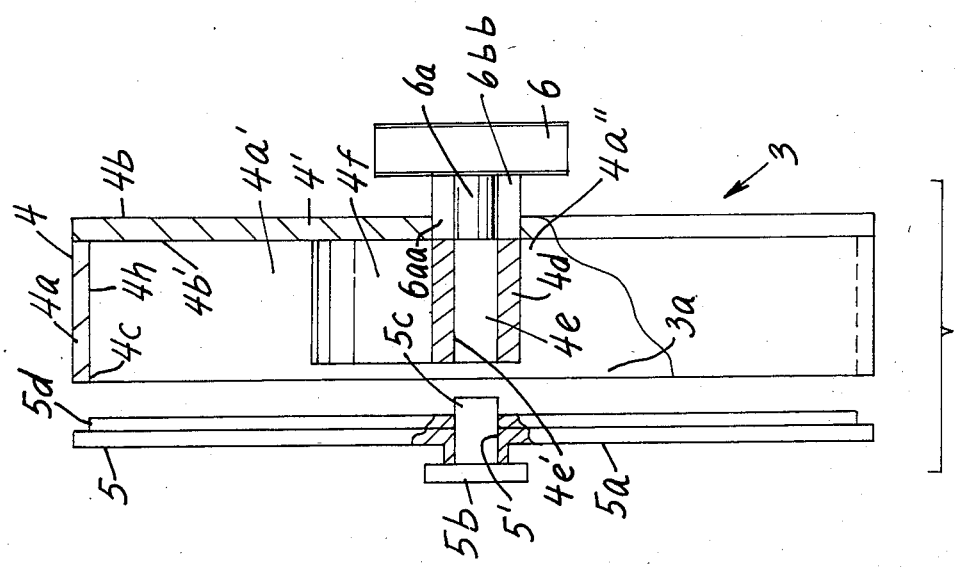

The dimensions of the apparatus of the invention as shown in FIGS. 1 and 2 may vary from large to small. However, special utility of the invention resides in the small and portable nature thereof, together with the shape and structure thereof making it adaptable for easy handling by removing the drum from the shaft 6a and its flanges of the driving motor 6 and thereafter placing it on a table or desk flatly whereby the lid would in that state be on top, and removing the lid for insertion or withdrawal of the separate samples of tablets to be tested or already tested.

In the FIG. 1 the lid 5 is illustrated in partial cut-away, and the partitioning walls 4f and 4g and female member 4d are shown in cross-section, and the circumscribing cylinder walls 4 are shown in partial cross-section, as well as the inside surface 4b' of the cylinder's end-wall 4b is shown beneath the cut-away portion. Formed within the cylinder are the separate segregated subspaces 8a and 8b. Partitioning wall-section 4f has concave surface 7a in subspace 8a, and convex surface 7a' in subspace 8b. Likewise, partitioning wall-section 4g has concave surface 7b in subspace 8b, and convex surface 7b' in subspace 8a. Inner surface 4e' of the female member 4d, forms space 4e in which the shaft 6a is inserted, and also in which the lid's male member 5c is insertable (see FIG. 2). The inserted mounting-shaft 6a may be seen in FIG. 1 as inserted within the space 4e (shown in FIG. 2). The subspaces 8a and 8b are further circumscribed by the inside surface 4h of the circumscribing cylinder walls 4. The partitioning walls each have central joining points 4f" with the female member 4d and the cylinder-walls joining points 4f'. The cylinder 3 revolves in direction 10 at a desired speed preferably sufficiently fast in rpm as to slide tablets within the subspace radially outwardly along the concave walls' surfaces 7a and 7b respectively such as tablets 9a, but below an rpm speed of rotation at which centrifugal forces would prevent the tablets from tumbling as illustrated by tumbling tablets 9b.

FIG. 2, apart from elements already identified in FIG. 1, illustrates the edge 4c of the cylinder's opening, and the lid's stepped structure 5d that detachably and securely wedges into the opening 3a of the cylinder. Also shown is the male member 5 that detachably and securely wedges into the space 4e of the female member 4d. After the cylinder 3 has been removed from the shaft 6 and its flanges 6aa and 6bb, and after it has been rested on its cylinder-end face 4b (as a bottom), the lid 5 is grasped by its handle 5b that is mounted in opening 5' of structure 5a, and is thereby lifted and separated from the cylinder 3 whereupon access is provable to each and both of the subspaces 8a and 8b.

The female member 4d is fixedly mounted onto the wall 4', central and coaxial to the axis of revolution of the cylinder 3 around the shaft 6a.

As a result of the two separate subspaces of the cylinder 3 with its top 5, separate sample of tablets from the same batch may be subjected to identical tumbling conditions, for exactly the same period of time and rate or revolution, etc., with a resulting final analysis of residual tablets after the tumbling, serving to provide back-up test results, one versus the other, with regard to either good or poor results, as the case may be, all readily ascertainable by the one single procedure of insertion concurrently into the separate segregated subspaces, and a single period of tumbling rotation of the drum (cylinder and top).

It is to be understood that any conventional drive motor with appropriate conventional switching is utilizable. However, the motor is preferably a variable speed motor, in order that speed of revolutions (rpm) may be set at desired and/or preferred levels for different types and compactions of the tablets, their compositions, etc.

It is within the scope of the invention to make such variations and substitution of equivalents, as would be apparent to a person of ordinary skill in this art.

While a novelty search was conducted, no relevant prior art was located, typical tablet testing apparatuses being shown in patents such as Smith U.S. Pat. No. 4,542,646 dated Sept. 24, 1985, and Melliger U.S. Pat. No. 3,618,395, and Flury U.S. Pat. No. 3,757,566 and Wilhelm, Jr. U.S. Pat. No. 3,943,757 and Barland U.S. Pat. No. 4,022,056.

We claim:

1. A pharmaceutical friability drum-tablet tester comprising in combination: drum means having circumscribing walls thereof forming a substantially total enclosure of enclosed space therein having a partitioning wall therein separating the space into at-least two separate sub-spaces totally isolated from each other, said partitioning wall extending in a direction parallel to an axis of rotation, and the drum means including port means for pharmaceutical tablet separate insertion into and withdrawal from said subspaces, said drum means being adapted to be revolvably supported and including said axis of rotation; and rotation means for causing said drum means to revolve around said axis of rotation.

2. A pharmaceutical friability drum-tablet tester according to claim 1, in which said circumscribing walls have inner surfaces, and in which said partitioning wall extends substantially through a center of said enclosed space and has opposite ends thereof mounted on substantially opposing spaced-apart portions of said inner surfaces.

3. A pharmaceutical friability drum-table tester according to claim 2, in which said drum means is shaped substantially as a cylinder and in which said partitioning wall extends substantially along a diameter of said cylinder a full height of said cylinder.

4. A pharmaceutical friability drum-tablet tester according to claim 1, in which substantially one-half end of said partitioning wall is convex and a remaining other one-half end of said partitioning wall is concave, such that the that the partitioning wall forms consecutive scoops of concave shape, one of the scoops being in one of said sub-spaces and the other of said scoops being in another one of said sub-spaces.

5. A pharmaceutical friability drum-tablet tester comprising in combination: drum means having circumscribing walls thereof forming a substantially total enclosure of enclosed space therein, having a partitioning wall therein separating the enclosed space into at-least two separate sub-spaces totally isolated from each other, and the drum means including port means for pharmaceutical tablet separate insertion into and withdrawal from said subspaces, said drum means including an open top vessel and a lid-closure structure adapted to detachably and sealably fit on and securably close said open top vessel, said open top vessel being inclusive of said circumscribing walls; and rotation means for causing said drum means to revolve.

6. A pharmaceutical friability drum-tablet tester according to claim 5, in which one of said rotation means and said drum means includes a first male member, and a remaining one of the rotation means and the drum means includes a first female member mateable with the first male member, said first male member and said first female member being detachably mated and having longitudinal axes thereof extending coaxially to said cylinder.

7. A pharmaceutical friability drum-tablet tester according to claim 6, in which said lid-closure structure includes one of a second male member and a second female member, and said cylinder at a cylinder end open to the lid-closure structure including a remaining one of said second male member and said second female member, adapted such that when mated, said lid is fastened securely onto and closing said cylinder.

8. A pharmaceutical friability drum-tablet tester according to claim 7, in which said rotation means includes a motor adapted to rotate said drum means around a height axis of the cylinder.

9. A pharmaceutical friability drum-tablet tester according to claim 8, in which said partitioning wall divides said enclosed space such that said cylinder is divided substantially equally into two of said subspaces.

10. A pharmaceutical friability drum-tablet tester according to claim 9, in which substantially one-half end of said partitioning wall is convex along one radius thereof and a remaining other one-half end of said partitioning wall is concave along a remaining radius thereof, forming consecutive scoops of concave shape in said partitioning wall, one of the scoops being in one of the sub-spaces and the other of said scoops being in a remaining other one of said sub-spaces.

* * * * *